(12) United States Patent
Nilsson et al.

(10) Patent No.: US 7,806,869 B2
(45) Date of Patent: Oct. 5, 2010

(54) BLOOD EXPOSURE PREVENTION IN VASCULAR ACCESS DEVICES

(76) Inventors: Anders Bengt Erik Nilsson, Sankt Peders gata 17, Helsingborg 254 37 (SE); Jörgen Bruno Hager, Jönköpingsgatan 83, Helsingborg 252 50 (SE); Kristoffer Glowacki, Breidablick 11, Staffanstorp 245 32 (SE); Karl Johan Mårten Söderholm, Harlyckegatan 5B, Helsingborg 256 58 (SE); Johan Fredrik Thörne, Norra Vallgatan 41, Helsingborg 252 34 (SE)

( * ) Notice: Subject to any disclaimer, the term of this patent is extended or adjusted under 35 U.S.C. 154(b) by 303 days.

(21) Appl. No.: 11/693,279

(22) Filed: Mar. 29, 2007

(65) Prior Publication Data
US 2008/0243092 A1  Oct. 2, 2008

(51) Int. Cl.
*A61M 5/178* (2006.01)
(52) U.S. Cl. .................................................. 604/164.01
(58) Field of Classification Search ..............................
604/164.01–164.04, 164.06–164.09, 192,
604/264, 93.01, 167.01, 167.03–167.04,
604/167.06, 168.01
See application file for complete search history.

(56) References Cited

U.S. PATENT DOCUMENTS

| | | | |
|---|---|---|---|
| 3,802,433 A | 4/1974 | Raven | |
| 4,231,367 A | 11/1980 | Rash | |
| 4,966,586 A | 10/1990 | Vaillancourt | |
| 5,030,205 A | 7/1991 | Holdaway et al. | |
| 5,092,845 A | 3/1992 | Chang | |
| 5,156,792 A | 10/1992 | Holdaway et al. | |
| 5,324,306 A * | 6/1994 | Makower et al. | 606/213 |
| 5,860,937 A | 1/1999 | Cohen | |
| 6,217,556 B1 * | 4/2001 | Ellingson et al. | 604/167.01 |
| 6,527,747 B2 * | 3/2003 | Adams et al. | 604/162 |
| 6,814,725 B2 | 11/2004 | Gutierrez | |
| 7,192,433 B2 | 3/2007 | Osypka et al. | |
| 7,238,169 B2 | 7/2007 | Takagi et al. | |

FOREIGN PATENT DOCUMENTS

EP  1 764 123 A1  3/2007

* cited by examiner

*Primary Examiner*—Nicholas D Lucchesi
*Assistant Examiner*—Christopher D Koharski
(74) *Attorney, Agent, or Firm*—Mony R. Ghose; Craig Metcalf; Kirton & McConkie

(57) ABSTRACT

An extravascular system includes a catheter assembly, a needle assembly, and a hemostatic adapter. The catheter assembly defines a lumen extending from a distal end thereof to a catheter hub at a proximal end thereof. The needle assembly includes a needle hub disposed at a proximal end of a needle disposed within the lumen defined by the catheter assembly. The hemostatic adapter defines a passage and is adapted to be operatively associated with the needle assembly and the catheter assembly. The hemostatic adapter-further includes at least one liquid-reactive material adapted to at least substantially seal the passage. The liquid-reactive material is selected and configured to morph upon contact with liquids to provide a mechanical barrier to prevent blood flow. A fluid may be injected into the lumen and/or passage by way of an optional port to provide a fluidic barrier in addition to the mechanical barrier.

16 Claims, 8 Drawing Sheets

BLOOD EXPOSURE PREVENTION IN VASCULAR ACCESS DEVICES

BACKGROUND

This disclosure relates generally to vascular access devices and methods, including catheter assemblies and devices used with catheter assemblies. Generally, vascular access devices are used for communicating fluid with the vascular system of patients. For example, catheters are used for infusing fluid, such as saline solution, various medicaments, and/or total parenteral nutrition, into a patient, withdrawing blood from a patient, and/or monitoring various parameters of the patient's vascular system.

Intravenous (IV) catheter assemblies are among the various types of vascular access devices and over-the-needle peripheral IV catheters are a common IV catheter configuration. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber, which is generally associated with a needle assembly. Once proper placement of the distal tip of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to house the tip of the needle in a secure location, thereby reducing the possibility of needle sticks when the needle and needle tip shield are separated properly from the catheter, which is left in place to provide intravenous access to the patient.

The separation of the needle assembly from the catheter portions of the catheter assembly presents numerous potential hazards to the clinicians and others in the area. As indicated above, there is a risk of accidental needle sticks if the needle tip is not secured properly in a needle tip shield. Additionally, between the time that the needle assembly is separated from the catheter portions and the time that the catheter portions are coupled to another medical device, such as an IV drip bag or pump machine, or are otherwise closed off, there is a risk that blood will exit from the catheter under the pressure of the patient's vascular system. Clinicians are very skilled at occluding the blood vessel through manual pressure and at the transition between removal of the needle assembly and closing the patient's vascular system through one or more of these techniques. Nevertheless, there is a risk that some blood may exit the system even in a perfect transition. For example, blood may follow the needle tip as the needle is withdrawn from the catheter and may splatter, splash, drip, or otherwise exit the proximal end of the catheter. Any blood flow from the proximal end of the catheter risks exposure to clinicians and is to be avoided.

The problem of unexpected and/or uncontrolled blood exposure during removal of the needle from the catheter is not new. Prior attempts to address this problem have universally relied upon some form of mechanical intervention to block fluid flow. For example, some prior systems have implemented a septum in the catheter hub surrounding the needle tip in an effort to create a closed system in the catheter. Other systems employ other modifications of the conventional catheter assembly to slow or limit blood flow in unintended manners, all of which include some mechanical means of restricting blood flow. While such mechanical solutions are effective to some degree, they can be complex and costly to manufacture. Additionally, such mechanical solutions often add energy to the system, such as the energy required to pull the needle through the septum. The added energy may result in splattering whatever blood does make it through the mechanical barrier. While certainly an improvement over systems without such mechanical blood flow restriction means, many, if not all, of the mechanical blockage systems have inherent leakages either through the design failing to create a perfect seal or through the operation of the mechanical system creating leaks through time delays. Accordingly, the problem of unexpected and/or uncontrolled blood exposure when introducer needles are removed from catheter assemblies remains to be solved. The present disclosure presents systems and methods to significantly limit and/or prevent such blood exposure.

BRIEF SUMMARY

The systems and methods of the present disclosure have been developed in response to problems and needs in the art that have not yet been fully resolved by currently available vascular access systems and methods. Thus, these systems and methods are developed to provide safer vascular access systems, methods of manufacturing the same, and methods of using the same to reduce blood exposure.

One aspect of the present disclosure provides an extravascular system for accessing the vasculature of a patient including safety features to reduce blood exposure and contamination. The extravascular system includes a catheter assembly, a needle assembly, and a hemostatic adapter. The catheter assembly has a proximal end and a distal end and includes a catheter and a catheter hub. The catheter includes an opening at the distal end of the catheter assembly and the catheter hub is disposed at the proximal end of the catheter assembly. The catheter assembly defines a lumen extending from the proximal end to the distal end. The needle assembly includes a needle that extends within the lumen defined by the catheter assembly. The hemostatic adapter is operatively associated with the catheter hub at the proximal end of the catheter assembly and defines a passage therethrough. The hemostatic adapter is also adapted to be operatively associated with the needle assembly. The hemostatic adapter includes at least one liquid-reactive material adapted to at least substantially seal the passage upon contact with one or more liquids.

The extravascular system may also include at least one port, a flush fluid supply and a flush fluid injector. When the extravascular system includes at least one port, the port(s) may be associated with one or more of the catheter assembly and the hemostatic adapter. The port may provide selective access to at least one of the lumen and the passage. The flush fluid supply that may be included in the extravascular system is adapted to contain flush fluid and to be operatively associated with at least one port. The flush fluid injector when included is operatively associated with the flush fluid supply and is adapted to inject the flush fluid into at least one of the lumen and the passage.

An extravascular system according to the present disclosure may be used to provide access to a subject's vasculature while minimizing the possibility of blood exposure. For example, an extravascular system may be provided including a catheter assembly, a needle assembly, and a hemostatic adapter. The catheter assembly defines a lumen extending from an opening at a distal end thereof to a catheter hub at a proximal end thereof. The needle assembly includes a needle hub disposed at a proximal end of a needle disposed within the lumen defined by the catheter assembly. The needle has a needle tip extending from the opening of the catheter assembly. The hemostatic adapter defines a passage and is operatively associated with the catheter hub and is operatively associated with the needle assembly. The hemostatic adapter includes at least one liquid-reactive material adapted to at least substantially seal the passage upon contact with one or more liquids. The extravascular system may be inserted into a selected vessel of a subject's vasculature such that the needle tip and the opening of the catheter assembly are in fluidic communication with the subject's vasculature and the needle may be withdrawn from the catheter assembly. Additionally, a liquid may be allowed to contact the liquid-reactive material in the hemostatic adapter to at least substantially seal the passage.

In some implementations, one or more ports may be associated with at least one of the catheter assembly and the hemostatic adapter providing selective access to at least one of the lumen and the passage. Moreover, a flush fluid injection assembly containing a flush fluid may be associated with at least one port. The liquid may be allowed to contact the liquid-reactive material before the extravascular system is inserted into the vasculature, after insertion but before removal of the needle is begun, and/or at any other time before the needle is completely withdrawn from the catheter assembly and the hemostatic adapter.

These and other features and advantages of the present disclosure may be incorporated into certain embodiments and will become more fully apparent from the following description and appended claims, or may be learned by the practice of the methods and use of the systems as set forth hereinafter. The present disclosure does not require that all the advantageous features and all the advantages described herein be incorporated into every embodiment.

BRIEF DESCRIPTION OF THE SEVERAL VIEWS OF THE DRAWINGS

In order that the manner in which the above-recited and other features and advantages of the disclosure are obtained will be readily understood, a more particular description will be rendered by reference to specific embodiments thereof which are illustrated in the appended drawings. These drawings depict only typical embodiments and are not therefore to be considered to limit the scope of the present disclosure.

DETAILED DESCRIPTION

The presently preferred embodiments of the present disclosure will be best understood by reference to the drawings. It will be readily understood that the components of the present disclosure, as generally described and illustrated in the figures herein, could be arranged and designed in a wide variety of different configurations. Thus, the following more detailed description, as represented in the figures, is not intended to limit the scope of the claims, but is merely representative of presently preferred embodiments.

Figure 1:
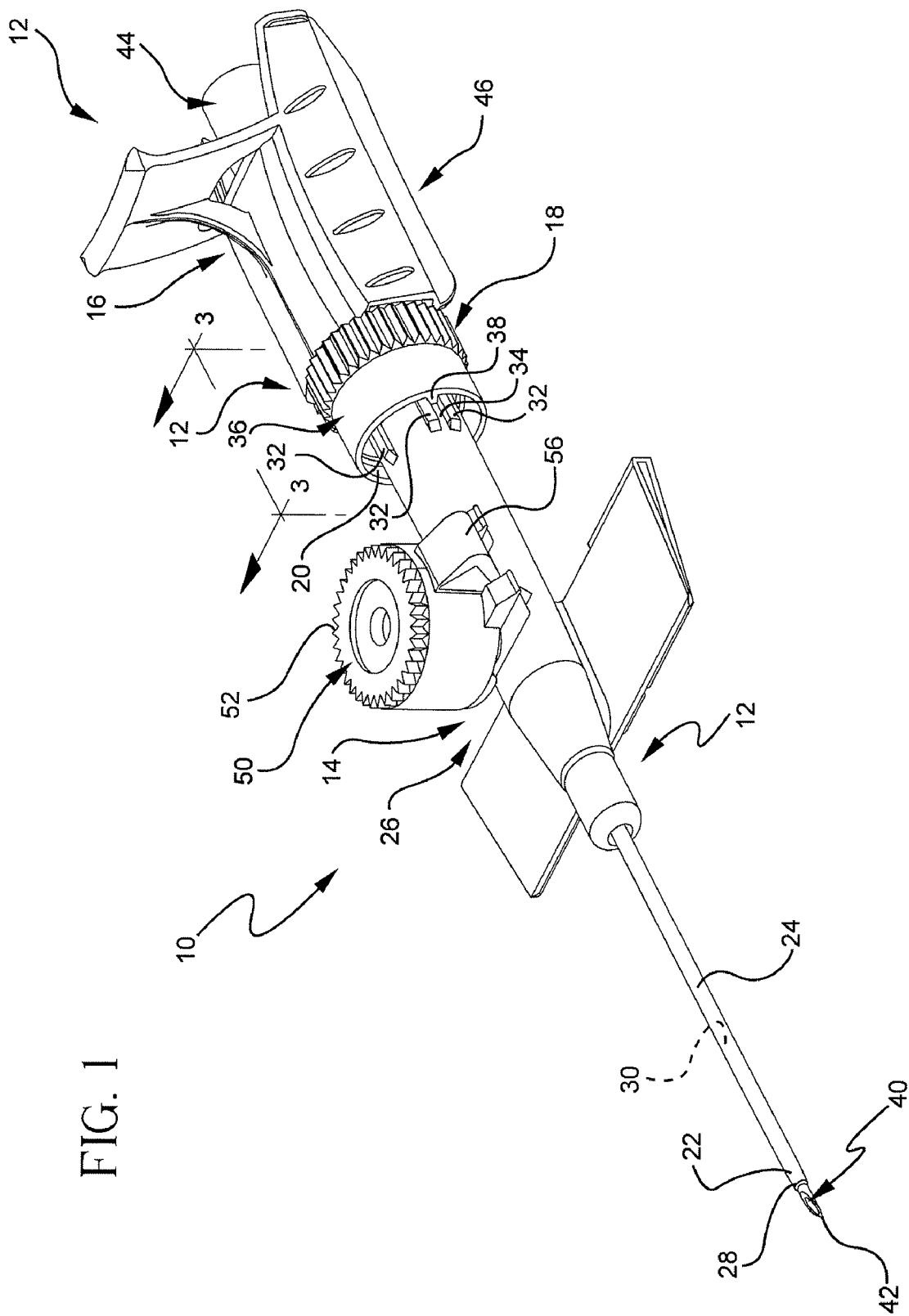
FIG. 1 is a perspective view of an extravascular system.

Referring to FIG. 1, a perspective view illustrates an example of an extravascular system 10 including multiple vascular access devices 12. In this example, the extravascular system 10 includes a catheter assembly 14, a needle assembly 16, and a hemostatic adapter 18. The catheter assembly 14 has a proximal end 20 and a distal end 22 and includes a catheter 24 having an opening 26 at the distal end 22 of the catheter assembly 14 and a catheter hub 28 disposed at the proximal end 20 of the catheter assembly. The catheter assembly 14 also defines a lumen 30 extending from the proximal end 20 to the distal end 22.

As illustrated, the catheter hub 26 includes a plurality of positioning ridges 32 and a positioning groove 34. The plurality of positioning ridges 32 and the positioning groove 34 are examples of coupling systems that may be used to position and/or retain another vascular access device, such as a closure mechanism 36, attached to the catheter hub 26 in a desired orientation. Other suitable coupling and positioning systems may be used. In the present illustration, the closure mechanism 36 is a hemostatic adapter 18 adapted to prevent blood from flowing from the proximal end of the catheter assembly 14. Coupling the closure mechanism 36 to the catheter hub 26 minimizes the risks of inadvertently dropping the closure mechanism 36 or contaminating the catheter hub 26. While the closure mechanism 36 is one exemplary configuration of a hemostatic adapter 18, other components may be configured to provide a hemostatic adapter 18. Additional detail regarding the closure mechanism 36 and the hemostatic adapter 18 will be provided below.

The hemostatic adapter 18 may be adapted to be selectively associated with the catheter assembly 14, for example by selective coupling and/or by fitting association. The hemostatic adapter 18 may be configured as a stand-alone component, such as the closure mechanism 36, or may be configured as a subcomponent of another component. When configured as a stand-alone component, the hemostatic adapter 18 may be selectively associated with another vascular access device 12 at the proximal end thereof. In the illustrative implementation of FIG. 1, the hemostatic adapter 18 in the form of a closure mechanism 36 is associated with the needle assembly 16 such that the closure mechanism 36 is disposed between the catheter assembly 14 and the needle assembly 16. The hemostatic adapter 18 may be configured to selectively couple to the needle assembly 16 and/or to be disposed in operative association therewith. One example of a hemostatic adapter 18 configured as a subcomponent of another component includes a needle tip shield, a subcomponent of a needle assembly, configured as a hemostatic adapter. For example, a needle cap 48 (described in more detail below) may be configured as a hemostatic adapter.

The needle assembly 16 includes a needle 40 that extends through the lumen 30 of the catheter assembly 14. As illustrated and conventional, the needle tip 42 extends through the opening 28 of the catheter 24. Additionally, the needle assembly 16 may include a variety of features to facilitate the insertion of the extravascular system into a patient's vasculature and the withdrawal of the needle 40 from the catheter assembly 14. For example, the needle assembly 16 may include a needle withdrawal assembly 44, which may include a needle hub 46 and a needle cap 48 (see FIG. 2). The needle assembly 16 of the present disclosure may incorporate one or more features from any of the presently available needle assemblies commonly used in vascular access devices or from needle assemblies still to be developed. For example, the needle assembly 16 may or may not include a needle cap 48 and the needle cap 48, when provided, be in any suitable configuration to reduce the risk of needle sticks. Regardless of the configuration of the needle assembly 16, the needle assembly will have a distal end adapted to associate with and/or to couple with the hemostatic adapter 18 and/or the catheter assembly 14.

FIG. 1 further illustrates an exemplary port 50 associated with the catheter hub 26 providing selective access to the lumen 30 of the catheter assembly 14. As illustrated, the port 50 includes a port cover 52 coupled to a port body 54 (seen better in FIG. 6) by a hinge 56. The port cover 52 and/or the port body 54 may include features to prevent fluid flow through the port except when desired. For example, the port body 54 may be provided with a septum (not shown) that can be opened by suitable devices but is biased to a closed position. Extravascular systems 10 according to the present disclosure may, in some implementations, include at least one port 50, which may be associated with the catheter assembly 14 and/or with the hemostatic adapter 18. The ports and their functionality will be more thoroughly discussed below.

Figure 2:
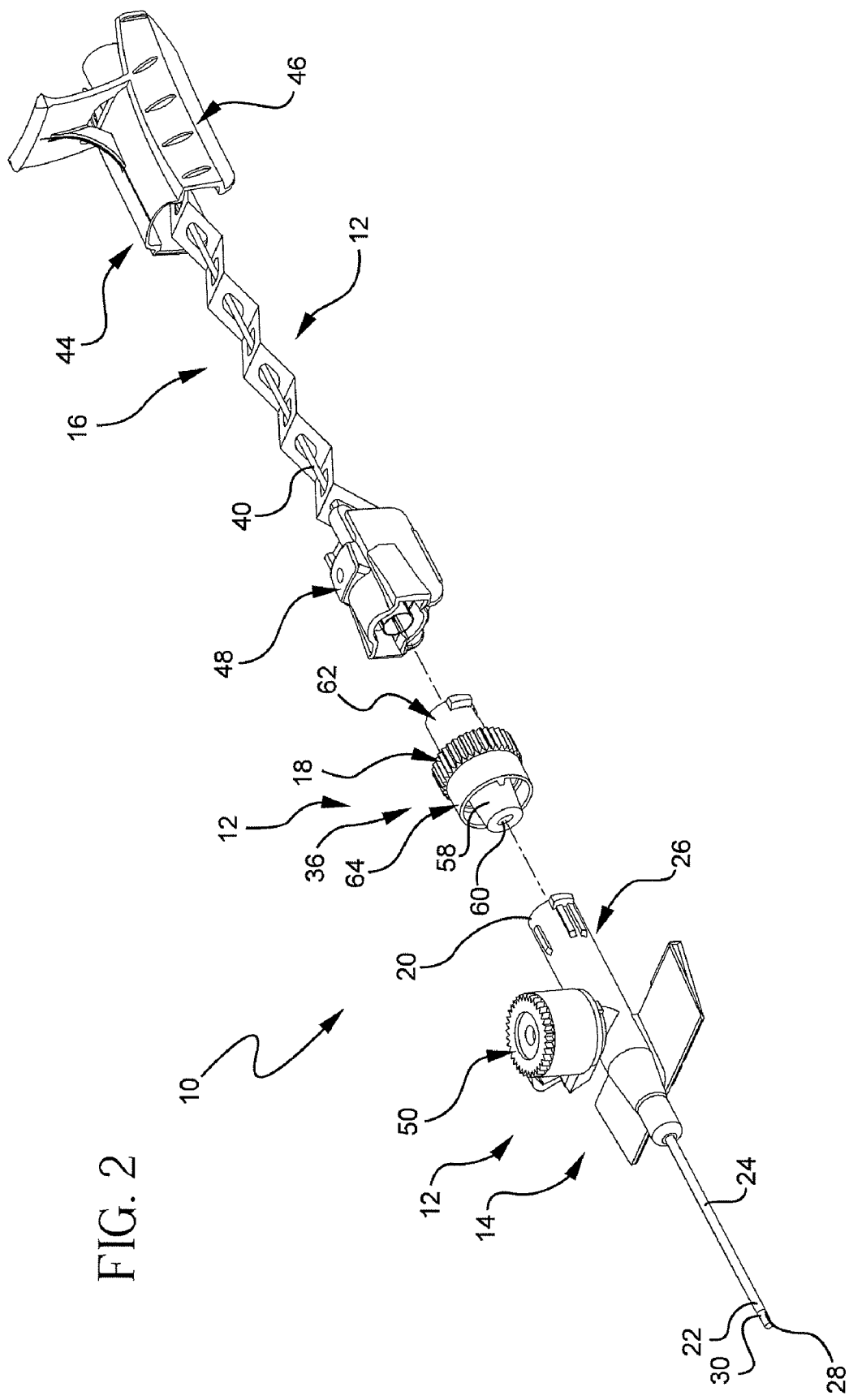
FIG. 2 is an exploded view of the extravascular system of FIG. 1.

Referring to FIG. 2, an exploded view of the extravascular system 10 of FIG. 1 shows the needle 40 withdrawn from the catheter 24 and the closure mechanism 36. As illustrated, the needle tip is drawn into the needle cap 48. As discussed above, the needle assembly need not include a needle cap 48 and the needle cap 48, when included, may be of any suitable configuration. As with conventional needle caps, needle caps 48 suitable for the present disclosure may include a shield capable of engaging or locking when the needle tip 42 is retracted beyond the shield. Once engaged or locked, the shield will prevent the needle tip 24 from re-emerging and extending beyond the shield and out of the needle cap 48. Continuing with the description of FIG. 2, the catheter assembly 14 is shown separated from the closure mechanism 36 to better illustrate the coupling features disposed at the proximal end of the catheter hub 26.

As introduced above, the closure mechanism 36 may include a hemostatic adapter 18 configured to control blood flow at the proximal end of the catheter assembly 14. The present hemostatic adapters 18 utilize a combination of mechanical and fluidic forces to control blood flow and thereby limit blood exposure. The hemostatic adapter 18 may include an enclosure 58 defining a passage 60 extending through the hemostatic adapter 18. Additionally, the hemostatic adapter 18 includes a proximal coupler 62 and a distal coupler 64. The coupler configuration selected for the distal end and/or the proximal end may vary depending on the intended application of the hemostatic adapter and may in some implementations include coupling features such as those illustrated in FIG. 2. In other implementations, the hemostatic adapter 18 may be configured to include distal and/or proximal ends adapted to merely associate with adjacent vascular access devices without coupling thereto. Additionally, as noted above, the hemostatic adapter 18 illustrated in FIG. 2 as a closure mechanism 36 is exemplary of suitable hemostatic adapters 18, which may include other configurations, such as a needle cap 48 configured as a hemostatic adapter.

With continuing reference to FIG. 2, it can be seen that the passage 60 through the hemostatic adapter 18 may be larger than the needle that extends through the passage. The exact diameter of the passage may vary in different implementations but preferably may be larger than the needle with which the hemostatic adapter 18 is to be used. In some implementations, it may be preferred to provide a passage 60 having a diameter sufficient to accommodate the largest gauge needle used by the manufacturer. Accordingly, a single product configuration could be manufactured for use in a variety of extravascular systems. Additionally, by providing an open passage that does not attempt to completely surround the needle shaft or otherwise retain the needle, assembly of the extravascular system is facilitated and force buildup is avoided to further minimize the risks of blood exposure.

Figure 3:
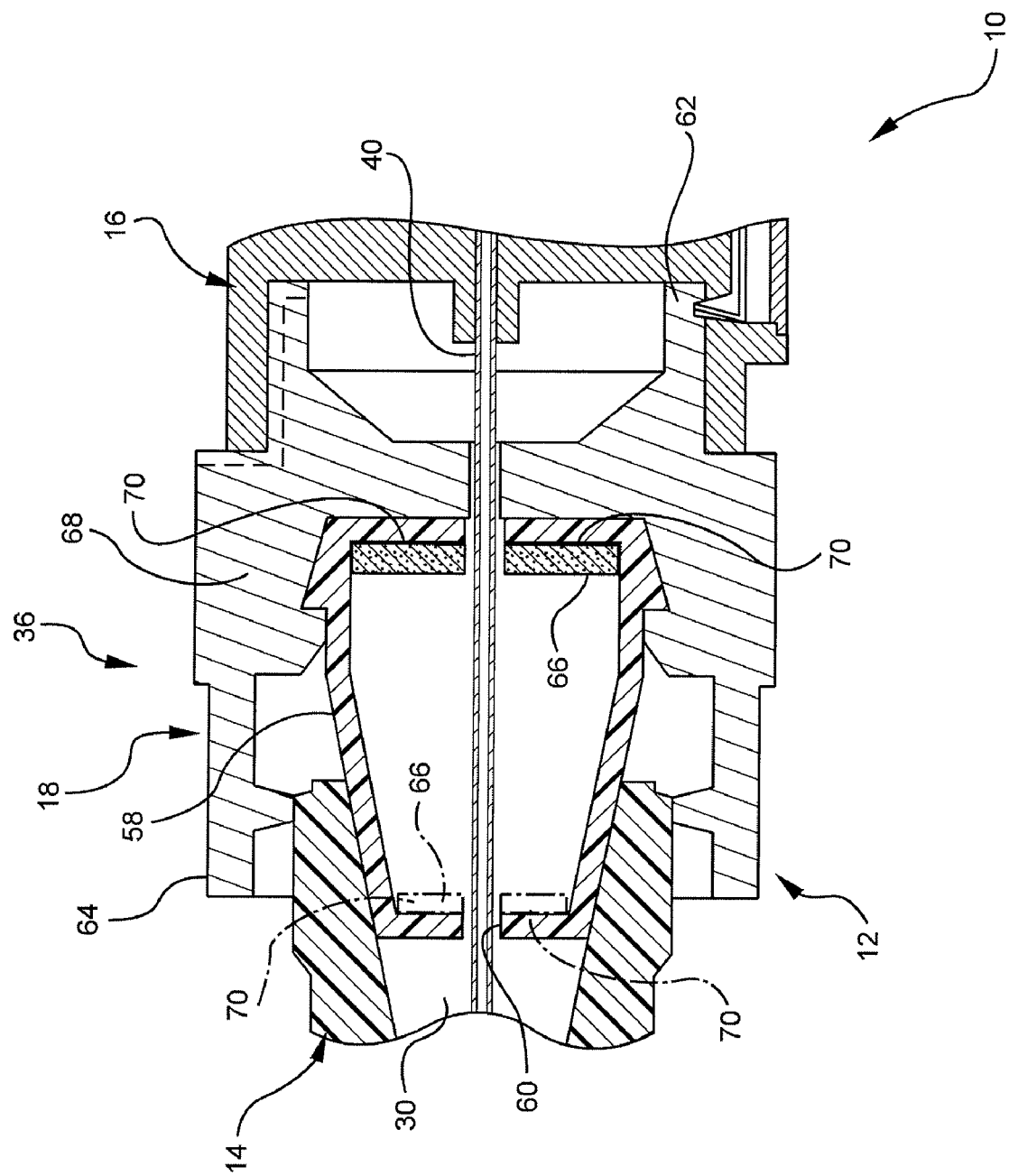
FIG. 3 is a cross-sectional view of a hemostatic adapter that may be incorporated into an extravascular system.

FIG. 3 illustrates a cross-sectional view of a portion of the extravascular system 10 taken along lines 3-3 in FIG. 1. As illustrated, the distal coupler 64 is coupled to the proximal end of the catheter assembly 14 and the proximal coupler 62 is coupled to the needle assembly 16. FIG. 3 further illustrates that the hemostatic adapter 18 may include an enclosure 58 distinct from the coupling elements of the hemostatic adapter. Alternatively, the enclosure and the coupling elements of the hemostatic adapter may be made of common materials and may be formed as an integral member. As illustrated, the coupling elements of the hemostatic adapter 18 and/or the enclosure 58 may be configured to facilitate the relationship with adjoining vascular access devices that comprise the extravascular system. FIG. 3 illustrates merely one configuration and relationship between the vascular access devices, other configurations may be suitable.

It should be understood that the enclosure 58 and the coupling elements of the hemostatic adapter 18 are optional and can be configured in any suitable manner to enable the hemostatic adapter to cooperate with the needle assembly and the catheter assembly. Regardless of these various configuration possibilities, hemostatic adapters 18 define a passage 60 extending from the proximal end to the distal end. Additionally, the hemostatic adapter 18 includes at least one liquid-reactive material 66 disposed in operative relationship to the passage 60. The liquid-reactive material 66 is selected and configured to provide an initially open passage 60 and to respond to contact with liquids by swelling or otherwise expanding to seal the passage 60 at least at one location within the passage. As one example, the liquid-reactive material 66 may absorb the liquid and thereby swell to occupy space in the passage 60 sufficient to seal the passage. In some configurations, the liquid-reactive material 66 may be disposed as a toroidal disc 70, such as shown in FIG. 3. Additionally or alternatively, the liquid-reactive material 66 may be provided in a configuration that is adapted to swell in predetermined patterns to swell in particular directions thereby sealing the passage 60 more efficiently. While absorption of liquids is one suitable means for causing the liquid-reactive material to respond to the liquid to seal the passage, other suitable mechanisms and materials may be used. For example, a coagulation mechanism, adsorption mechanism, or other solidification mechanism may be used to seal the passage 60.

Examples of suitable absorbent materials that may be used include micro-porous polysaccharide hemispheres, sodium polyacrylate, purified pork skin gelatin, and carboxy methyl cellulose. Examples of suitable coagulant materials include oxidized regenerated cellulose, microfibrillar collagen, topical thrombin, and fibrin sealants. It should be noted that some materials may act as both an absorbent and a coagulant, such as by absorbing only the moisture in the blood to accelerate clotting, whereas others may act as pure absorbents absorbing the blood to form a gel. While the above materials may be suitable, other materials may be used as well as combinations of materials.

As illustrated, the liquid-reactive material is disposed within the enclosure 58. Additionally or alternatively, the liquid-reactive material may be disposed on the exterior of the enclosure 58 or in operative relationship with the adapter body 68. The liquid-reactive material 66 may be disposed in any suitable relationship with the hemostatic adapter such that the material is caused to seal the passage 60 when it is contacted by a liquid. The materials selected for the liquid-reactive material and the configuration of the material may be selected to provide a predetermined time lapse between initial contact with a liquid and sealing of the passage or to require a particular volume of liquid to contact the material before the passage is sealed. It may be preferred to minimize the time lapse and the volume of liquid required. Accordingly, it should be understood that as used herein, references to liquid-reactive materials sealing upon contact with liquid or when contacted by liquid are intended to indicate that the liquid-reactive material begins to react to the liquid upon contact with the liquid or very soon thereafter, which time period may be customized depending on the desired operating parameters. Similarly, the time from initial reaction to substantial sealing of the passage may be varied according to the desired operating conditions.

Figure 5:
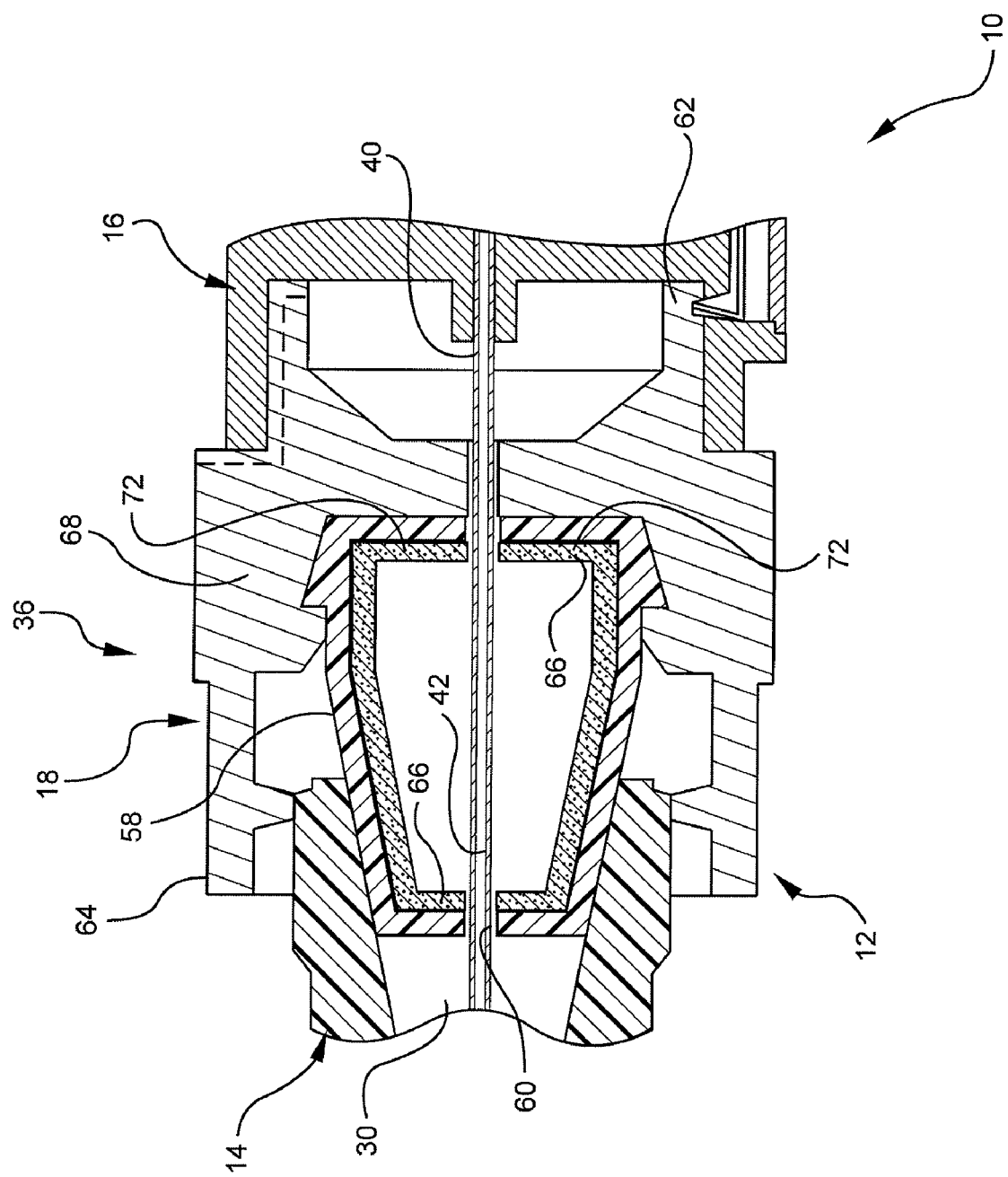
FIG. 5 is another cross-sectional view of a hemostatic adapter that may be incorporated into an extravascular system.

With continuing reference to FIG. 3 and with reference to FIG. 5, at least two possible configurations of the liquid-reactive material are illustrated. To the extent that FIG. 5 illustrates elements identical to those of FIG. 3, corresponding reference numerals are used. As seen in FIG. 3, two toroidal discs 70 are disposed within the enclosure 58 at opposing ends of the passage 60 within the enclosure. As illustrated, the distal disc 70 is optional but may be included to provide additional functionality to the hemostatic adapter 18. For example, closing the distal end as well as the proximal end may provide a fully closed passage within the hemostatic adapter such that the hemostatic adapter 18 may be decoupled from the catheter assembly with reduced risk of exposure from the proximal or distal ends. In the illustrated example of FIG. 3, the use of two toroidal discs 70 at opposing ends of the passage 60 may effectively seal off the passage to enclose whatever fluids may be left behind after the needle is withdrawn. Additionally, the two discs 70 provide a layer of redundancy to further reduce the risk of blood exposure from blood exiting the proximal end of the catheter assembly. FIG. 5 similarly illustrates liquid-reactive material 66 disposed within the enclosure 58 and at opposing ends of the passage. The liquid-reactive material in FIG. 5 is configured as an elongate washer 72. The elongate washer configuration may enable the liquid-reactive material at the proximal end of the passage 60 to begin swelling or otherwise sealing the proximal end before liquid actually reaches the proximal end. As discussed above, other suitable configurations may be selected for the liquid-reactive material 66 provided that the material will be able to react to contact with liquid to at least substantially seal the passage 60.

Figure 4:
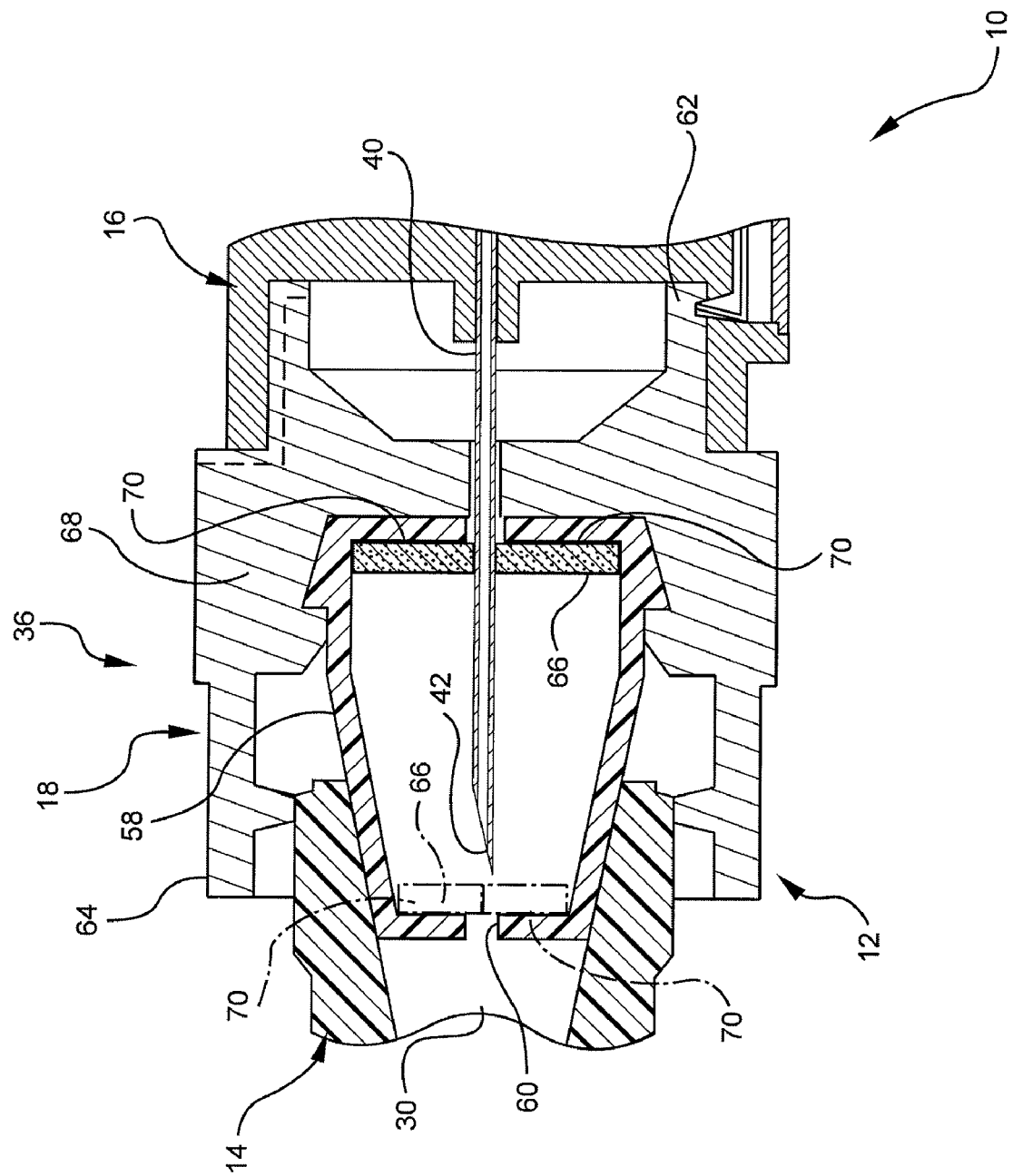
FIG. 4 is another cross-sectional view of a hemostatic adapter that may be incorporated into an extravascular system.

For purposes of illustration, FIG. 4 provides a representation of the hemostatic adapter 18 after the liquid-reactive material 66 has been contacted by a liquid and caused to seal the passage 60. As illustrated, the needle 40 is partially withdrawn from the catheter assembly 14 such that the needle tip 42 is disposed within the hemostatic adapter 18. The illustrated hemostatic adapter 18 includes liquid-reactive material 66 in the form of a toroidal disc 70 at the distal end of the passage 60 that has sealed to close the passage. Additionally, the liquid-reactive material 66 has sealed around the needle 40 at the proximal end of the passage 60. The sealed toroidal disc 70 at the distal end of the hemostatic adapter 18 may provide multiple functions. For example, when the hemostatic adapter is coupled to the catheter assembly 14, the sealed toroidal disc 70 may prevent blood from exiting the catheter assembly. Additionally, when the hemostatic adapter 18 is provided with a liquid-reactive material 66 at the distal end thereof may assist in preventing fluids from exiting the hemostatic adapter once the hemostatic adapter is disconnected from the catheter assembly.

Figure 6:
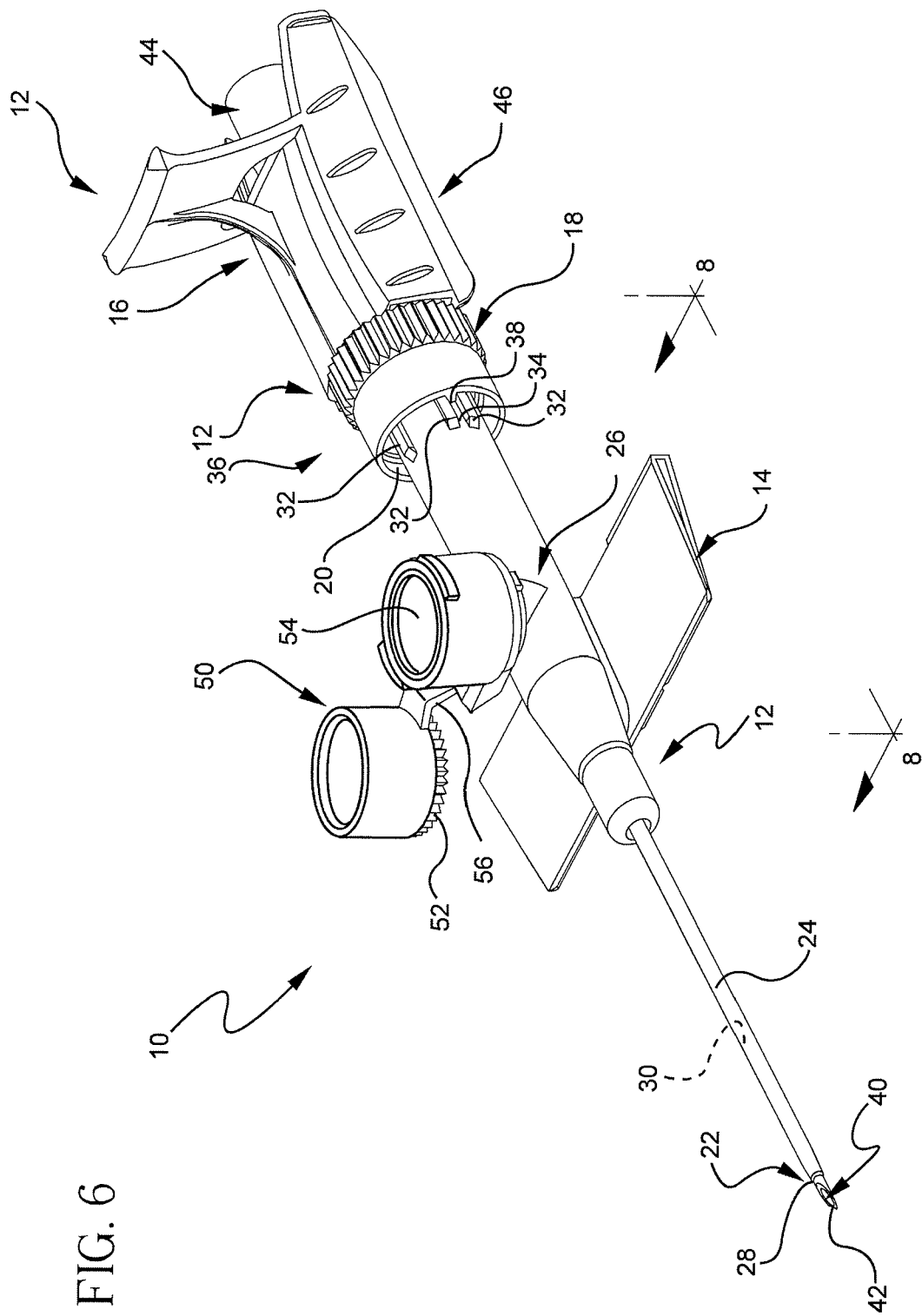
FIG. 6 is another perspective view of an extravascular system according to the present disclosure.
Figure 7:
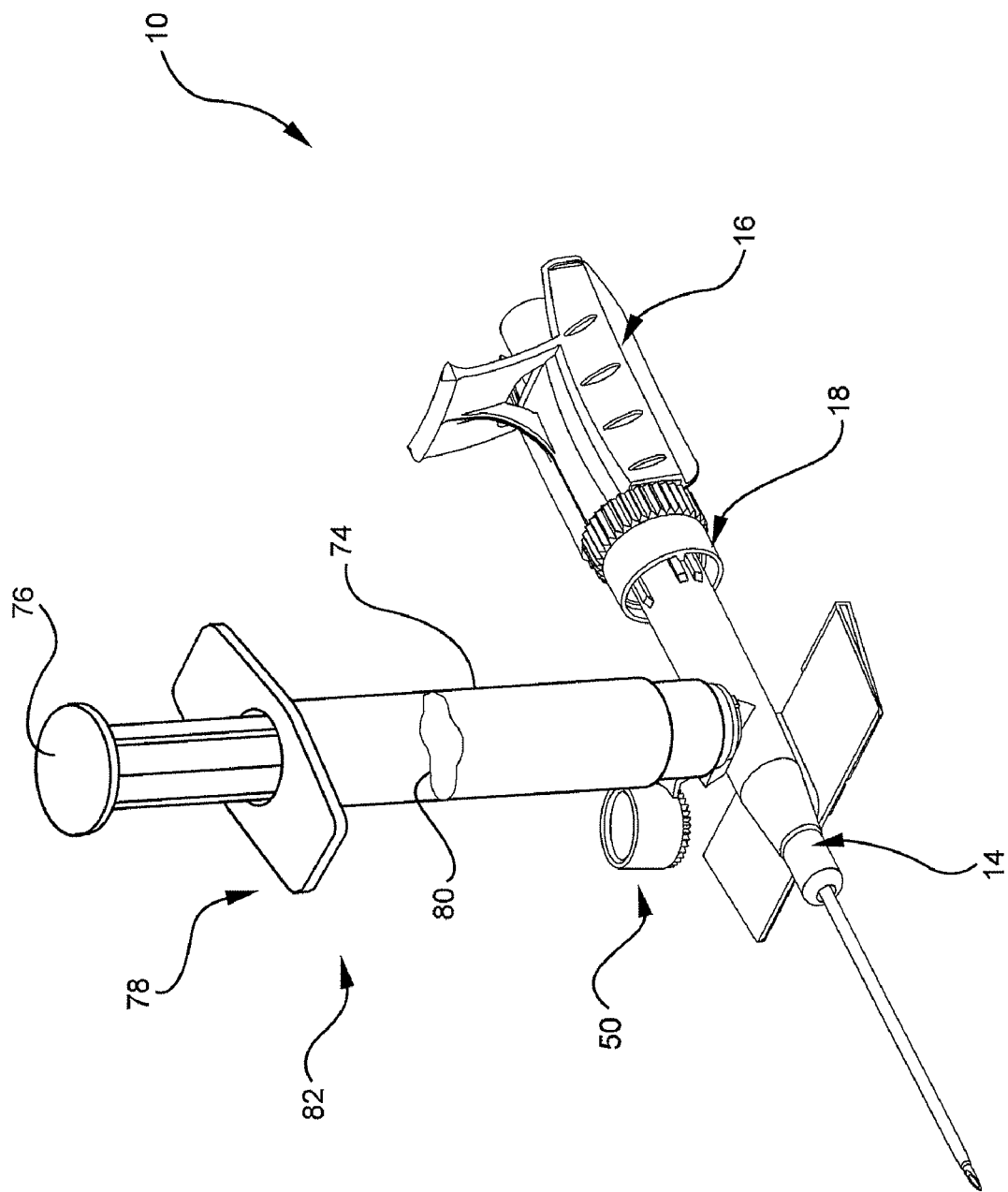
FIG. 7 is a perspective view of an extravascular system including a flush fluid injection assembly.

FIGS. 6 and 7 provide additional perspective views of extravascular systems 10 within the scope of the present disclosure. FIG. 6 illustrates the extravascular system 10 of FIG. 1 including the port 50 and showing the port cover 52 in the open configuration revealing the port body 54. As illustrated, the port 50 is a component of the catheter assembly 14 and provides access to the lumen 30 of the catheter assembly. Additionally or alternatively, a port, which may be similar to the illustrated port 50, may be associated with the hemostatic adapter 18. As discussed above, the hemostatic adapter 18 includes a liquid-reactive material 66. The port 50 may be used to inject a liquid to trigger the sealing of the passage 60 by the liquid-reactive material 66. As will be discussed in more detail below, the sealing by the liquid-reactive material 66 may be triggered by blood entering the lumen of the catheter and/or by contact with another fluid injected into the lumen of the catheter and/or the passage of the hemostatic adapter. By injecting a liquid through a port 50, the hemostatic adapter 18 may be primed before blood is allowed to enter the lumen of the catheter by withdrawal of the needle 50. That is, the liquid-reactive material may be caused to seal the passage of the hemostatic adapter 18 before blood enters the lumen.

For example, in some implementations the passage 60 may be open while the needle 40 is passed through the hemostatic adapter 18 to facilitate the operation. The hemostatic adapter 18 may then be primed, such as by injection of a flush fluid 80 into the passage 60, to substantially seal the passage 60 around the needle 40 before the extravascular system is inserted into the patient's vasculature. In other implementations, the flush fluid 80 may be injected into the passage 60 and/or the lumen 30 during the insertion of the extravascular system into the patient or at another time before blood reaches the hemostatic adapter. Additionally or alternatively, the liquid-reactive material 66 in the hemostatic adapter 18 may respond to a combination of the flush fluid 80 and blood from the patient's vasculature alone depending on the timing of the flush fluid injection. Still additionally or alternatively, in implementations that omit the optional port 50, the liquid-reactive material 66 may react to contact with the patient's blood.

FIG. 7 illustrates one exemplary flush fluid supply 74 and an exemplary flush fluid injector 76 that may be utilized with the remaining components of the extravascular systems. As illustrated, the flush fluid supply 74 and flush fluid injector 76 may be provided by an external syringe 78 adapted to be coupled to the port 50 and/or to be in fluid communication with the port 50. The flush fluid supply 74 may be adapted to store any suitable flush fluid 80, such as a saline solution or other solutions that are non-hazardous to clinicians or patients. The flush fluid supply 74 may be adapted to store a predetermined volume of flush fluid and/or to dispense a predetermined volume of flush fluid 80.

While not illustrated, it should be understood that the flush fluid supply 74 and the flush fluid injector 76 may be configured in any suitable manner and may include conventional or yet to be developed devices. For example, any suitable flush fluid injection assembly 82 may be operatively associated with the catheter assembly 14, the needle assembly 16, and/or the hemostatic adapter 18 to store a supply of flush fluid and to cause the flush fluid to be injected into one or more of the lumen and the passage. Some implementations may incorporate one or more components of the flush fluid injection assembly 82 in the needle assembly 16. For example, a laterally disposed flush fluid supply and injector may be disposed along the needle hub 46. Such a configuration may facilitate the activation of the flush fluid injection assembly while controlling the remaining aspects of the extravascular system 10. For example, it may be desirable to inject the flush fluid into the lumen and/or passage while withdrawing the needle 40 from the catheter assembly 14 and having the flush fluid injector within reach of the needle hub 46 may facilitate such coordination.

Additionally or alternatively, one or more of the needle assembly 16, the catheter assembly 14, and the hemostatic adapter 18 may be configured to provide a needle stop. The needle stop may be provided by corresponding notches and detents in adjoining members. Additionally or alternatively, a needle stop may be provided by the needle withdrawal assembly 44, such as by creating a place of increased resistance to release of the tether between the needle hub and the needle cap. Suitable needle stops need not provide an actual stop to the withdrawal of the needle and may provide some form of tactile feedback to indicate to the user that the needle has reached a particular point in the withdrawal process. The location and implementation of the needle stop may be configured and selected to indicate to the user that the flush fluid should be injected before continuing to withdraw the needle from the catheter assembly 14.

Still additionally or alternatively, the flush fluid injection assembly 82 may be adapted to coordinate the injection of the flush fluid with the withdrawal of the needle. For example, the injection assembly 82 and the needle withdrawal assembly 44 may be associated and/or synchronized such that the same action that withdraws the needle also injects the flush fluid at a rate appropriate for the withdrawal rate.

Figure 8:
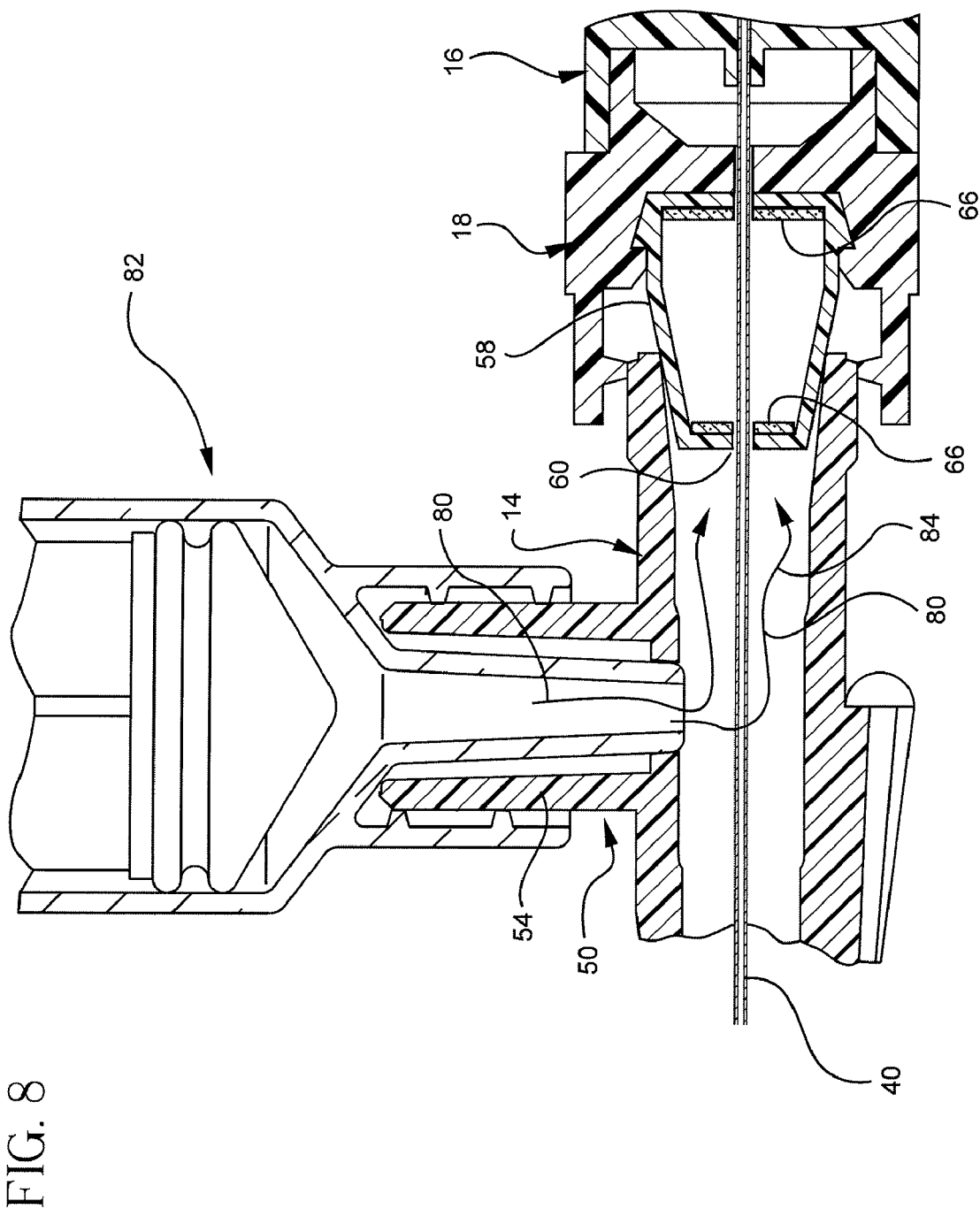
FIG. 8 illustrates an extravascular system within the scope of the present disclosure showing a method of using the same.

Many aspects of the use and implementation of extravascular systems 10 within the scope of the present disclosure have been described above or can be discerned from the foregoing description. FIG. 8 presents a cross-sectional view of a portion of the catheter assembly 14, the hemostatic coupler 18, and the needle assembly 16 together with an associated flush fluid injection assembly 82 to illustrate methods of using the extravascular systems 10. As illustrated, the needle 40 is disposed in the lumen 30 of the catheter assembly 14 and in the passage 60 of the hemostatic adapter 18. The liquid-reactive material 66 is disposed in the passage 60 and is beginning to expand to seal around needle 40. FIG. 8 further illustrates the flush fluid 80 being injected into the lumen 30 and progressing toward the hemostatic adapter 18, as represented by arrows 84. As discussed above, the opening 28 of the catheter is generally tightly adjoining the exterior surface of the needle 40 to prevent peelback of the catheter. Accordingly, flush fluid injected into the lumen before the needle is withdrawn will be directed to the hemostatic adapter 18. Moreover, the pressure of the blood from the subject's vasculature will move the flush fluid 80 toward the hemostatic adapter 18 should the seal between the catheter opening 28 and the needle 40 be broken through withdrawal of the needle or otherwise.

Once the flush-fluid 80 is injected into the lumen 30 (or is injected into the passage 60 of the hemostatic adapter), the liquid of the flush fluid causes the liquid-reactive material 66 to begin to swell or otherwise morph to seal the passage 60. In some methods of using the extravascular systems 10 of the present disclosure, the flush fluid 80 may be injected into the lumen 30 and/or passage 60 to prime the hemostatic adapter 18 to seal the passage 60 before blood is allowed to enter the lumen 30 of the catheter assembly 14. Accordingly, in some implementations, the flush fluid 80 may be injected into the lumen 30 and/or the passage 60 prior to inserting the extravascular system 10 into a subject's vasculature. Additionally or alternatively, the flush fluid 80 may be injected into the lumen 30 and/or passage 60 after the extravascular system has been inserted into the subject's vasculature but before the clinician has begun to withdraw the needle from the catheter assembly 14. Still additionally or alternatively, the flush fluid 80 may be injected while the needle assembly is being withdrawn. Moreover, it should be understood that some implementations of the flush fluid injection assembly 82 and the flush fluid 80 may be omitted entirely and the liquid-reactive material 66 may react to contact with blood.

The combination of the flush fluid injection assembly 82 and the hemostatic adapter 18 including a liquid-reactive material 66 provides at least two barriers to blood leakage or exposure. As described above, the liquid-reactive material 66 may provide at least one seal to prevent blood from flowing through the passage. Additionally, when a flush fluid 80 is injected into the lumen 30 and/or passage 60, the flush fluid itself presents a barrier to blood flow in that the flush fluid will exit the lumen of the catheter prior to any blood. For example, when the flush fluid 80 is injected into the lumen of the catheter, the flush fluid may cause the liquid-reactive material to seal the passage 60 while flush fluid 80 remains in the lumen surrounding the needle. Accordingly, the flush fluid 80 in the lumen may provide a fluidic barrier to blood flow as the needle is withdrawn from the catheter assembly in addition to the mechanical barrier formed by the liquid-reactive material 66. Once the needle assembly is separated from the catheter assembly and the hemostatic adapter, the hemostatic adapter 18 may be decoupled from the catheter assembly to allow other vascular access devices to be coupled to the catheter assembly 14. The transition between the hemostatic adapter and the subsequent vascular access device may be accompanied by conventional manual occlusion of the blood vessel. However, manual occlusion is an imperfect art and some blood may pass the manual occlusion. The complimentary fluidic blockage provided by the flush fluid in the catheter lumen further protects the clinician by causing any pressure passing by the manual occlusion to eject flush fluid rather than blood. Moreover, the fluidic blockage provided by the flush fluid in the lumen may prevent blood from contacting the hemostatic adapter, which may further reduce the risk of exposure.

It is believed that the disclosure set forth above encompasses multiple distinct methods and/or apparatus with independent utility. While each of these methods and apparatus has been disclosed in its preferred form, the specific embodiments thereof as disclosed and illustrated herein are not to be considered in a limiting sense as numerous variations are possible. The subject matter of the disclosures includes all novel and non-obvious combinations and subcombinations of the various elements, features, functions and/or properties disclosed herein. The principles of the present disclosure may be embodied in other specific forms without departing from its structures, methods, or other essential characteristics as broadly described herein. The described embodiments are to be considered in all respects only as illustrative, and not restrictive. The scope of the disclosure is, therefore, not limited by the foregoing description or the following claims, and all changes that come within the meaning and range of equivalency of the foregoing description and/or the following claims are to be embraced within its scope. Similarly, where the description and/or the claims recite "a" or "a first" element or the equivalent thereof, such description should be understood to include incorporation of one or more such elements, neither requiring nor excluding two or more such elements.

It is believed that the following claims are directed to certain combinations and subcombinations that correspond to disclosed examples and that are believed to be novel and non-obvious. Other combinations and subcombinations of features, functions, elements and/or properties may be claimed through amendment of the present claims or presentation of new claims in this or a related application. Such amended or new claims, whether they are directed to a different combination or directed to the same combination, whether different, broader, narrower or equal in scope to the original claims, are also regarded as included within the subject matter of the present disclosure.

The invention claimed is:

1. An extravascular system for accessing the vasculature of a patient, comprising:
   a catheter assembly having a proximal end and a distal end and having a catheter and a catheter hub; wherein the catheter includes an opening at the distal end of the catheter assembly; wherein the catheter hub is disposed at the proximal end of the catheter assembly; wherein the catheter assembly defines a lumen extending from the proximal end to the distal end;
   a needle assembly including a needle, wherein the needle extends within the lumen defined by the catheter assembly; and
   a hemostatic adapter defining an enclosure and a passage therethrough, the hemostatic adapter operatively associating with the catheter assembly and the needle assembly, and the hemostatic adapter including a liquid-reactive material disposed within the enclosure.

2. The system of claim 1, further comprising:
   at least one port associated with at least one of the catheter assembly and the hemostatic adapter providing selective access to at least one of the lumen and the passage;
   a flush fluid supply containing flush fluid and operatively associated with at least one port; and
   a flush fluid injector operatively associated with the flush fluid supply and adapted to inject the flush fluid into at least one of the lumen and the passage.

3. The system of claim 2, wherein the flush fluid supply and the flush fluid injector includes an external syringe, and wherein the at least one port is adapted to selectively couple to the external syringe.

4. The system of claim 2, wherein at least one of the flush fluid supply and the flush fluid injector are operatively coupled to one or more of the catheter assembly, the needle assembly, and the hemostatic adapter.

5. The system of claim 1, wherein the needle assembly comprises the needle and a needle withdrawal assembly including a needle hub; wherein the needle comprises a needle tip distal from the needle hub; wherein the needle is withdrawn from the catheter assembly by separating the needle hub from the catheter assembly until the needle tip exits the catheter lumen; and wherein the needle assembly provides a needle stop triggered during the withdrawal process prior to the exit of the needle tip from the catheter lumen.

6. The system of claim 2, wherein the needle assembly comprises the needle and a needle withdrawal assembly including a needle hub; wherein the needle comprises a needle tip distal from the needle hub; wherein the needle is withdrawn from the catheter assembly by separating the needle hub from the catheter assembly until the needle tip exits the catheter lumen; and wherein the needle assembly and the flush fluid injector are operatively associated to inject the flush fluid into at least one of the lumen and the passage during withdrawal of the needle from the catheter lumen.

7. The system of claim 6, wherein the needle assembly and the flush fluid injector are operatively associated to inject the flush fluid into at least one of the lumen and the passage when the needle tip is in a predetermined range of positions while withdrawing the needle from the catheter lumen.

8. The system of claim 1, wherein the at least one liquid-reactive material is adapted to seal the passage around the needle at a proximal end of the hemostatic adapter to prevent one or more fluids from exiting the catheter assembly as the needle is withdrawn from the catheter assembly.

9. The system of claim 8, wherein the at least one liquid-reactive material is adapted to seal the passage at a distal end of the hemostatic adapter to prevent one or more fluids from exiting the hemostatic adapter distally.

10. The system of claim 1, wherein the hemostatic adapter is primed by the flush fluid to at least substantially seal the passage prior to insertion of the needle into a patient's vasculature.

11. The system of claim 1, wherein the needle assembly further includes a needle cap, and wherein the hemostatic adapter is configured as the needle cap.

12. A method of manufacturing an extravascular system, comprising:
   providing a catheter assembly having a catheter lumen defined through the catheter assembly and having a catheter hub at a proximal end of the catheter assembly and a catheter opening at a distal end of the catheter assembly;
   providing a hemostatic adapter defining a passage therethrough and adapted to associate with the proximal end of the catheter assembly and with a needle assembly, the hemostatic adapter having an enclosure, wherein the hemostatic adapter further includes a liquid-reactive material disposed within the enclosure;
   associating the hemostatic adapter on the proximal end of the catheter assembly;
   providing a needle assembly having a needle and a needle hub; and
   associating the needle assembly with the catheter assembly and the hemostatic adapter such that the needle extends through the passage of the hemostatic adapter and the catheter lumen.

13. The method of claim 12, wherein at least one of the hemostatic adapter and the needle assembly is adapted to cooperate with the other to provide a needle stop.

14. The method of claim 12, wherein at least one of the catheter assembly and the hemostatic adapter includes a port providing access to one or more of the catheter lumen and the adapter passage; and wherein the method further comprises providing a flush fluid injection assembly adapted to be disposed in fluidic communication with at least one port during use of the extravascular assembly.

15. The method of claim 14, wherein the flush fluid injection assembly includes a flush fluid supply containing a flush fluid and wherein the flush fluid injection assembly is operatively coupled to one or more of the catheter assembly, the hemostatic adapter, and the needle assembly to inject the flush fluid into at least one of the adapter passage and the catheter lumen when the needle is withdrawn from the catheter assembly.

16. An extravascular system comprising:
   a catheter assembly, wherein the catheter assembly defines a lumen extending from an opening at a distal end thereof to a catheter hub at a proximal end thereof;
   a needle assembly, wherein the needle assembly includes a needle hub disposed at a proximal end of a needle, the needle being disposed within the lumen defined by the catheter assembly;
   a hemostatic adapter defining a passage and being disposed between the catheter assembly and the needle hub when the needle is inserted through the passage, the hemostatic adapter including a liquid-reactive material coupled to an interior surface of the hemostatic adapter; and
   a port, wherein the port is associated with at least one of the catheter assembly and the hemostatic adapter, the port providing selective access to at least one of the lumen and the passage.

* * * * *